United States Patent
Vasko

(10) Patent No.: US 9,731,105 B2
(45) Date of Patent: Aug. 15, 2017

(54) MICRO INFUSION DEVICE FOR DRUG DELIVERY

(71) Applicant: CareFusion 303, Inc., San Diego, CA (US)

(72) Inventor: Robert Vasko, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 14/627,557

(22) Filed: Feb. 20, 2015

(65) Prior Publication Data

US 2016/0243346 A1 Aug. 25, 2016

(51) Int. Cl.
| | |
|---|---|
| *A61M 39/02* | (2006.01) |
| *A61M 39/28* | (2006.01) |
| *A61M 39/24* | (2006.01) |
| *A61M 39/10* | (2006.01) |

(52) U.S. Cl.
CPC ...... *A61M 39/0208* (2013.01); *A61M 39/286* (2013.01); *A61M 2039/1083* (2013.01); *A61M 2039/1088* (2013.01); *A61M 2039/2473* (2013.01)

(58) Field of Classification Search
CPC .... A61M 39/0208; A61M 2005/14208; A61M 5/142; A61M 39/286; A61M 2039/1083; A61M 2039/1088; A61M 2039/2473
See application file for complete search history.

(56) References Cited

U.S. PATENT DOCUMENTS

| | | | | |
|---|---|---|---|---|
| 4,457,752 | A | * 7/1984 | Vadasz | A61M 5/14276 604/135 |
| 5,267,964 | A | * 12/1993 | Karg | A61M 5/1424 604/141 |
| 5,967,484 | A | 10/1999 | Morris | |
| 6,360,784 | B1 | * 3/2002 | Philippens | A61M 5/1407 141/2 |

(Continued)

FOREIGN PATENT DOCUMENTS

| | | |
|---|---|---|
| EP | 77604 B1 | 6/1986 |
| GB | 1333096 A | 10/1973 |

(Continued)

OTHER PUBLICATIONS

International Search Report issued in International Application No. PCT/US2016/018414, mailed May 19, 2016.

*Primary Examiner* — Emily Schmidt
*Assistant Examiner* — Lauren M Peng
(74) *Attorney, Agent, or Firm* — Mintz Levin Cohn Ferris Glovsky and Popeo, P.C.

(57) ABSTRACT

A device introduced small volumes of fluid for delivery to a patient through a fluid line. The device includes a first arm adapted to receive a syringe and a second arm fluidly connected to an upstream reservoir that defines an internal volume adapted to receive a volume of fluid. The device includes a fluid obstruction mechanism configured to selectably block flow of fluid from the reservoir toward the patient, wherein the fluid obstruction mechanism transitions between a first state that permits fluid flow from the reservoir toward the patient and a second state that directs fluid flow from the syringe into the reservoir while blocking fluid flow from the reservoir toward the patient.

15 Claims, 10 Drawing Sheets

(56) References Cited

U.S. PATENT DOCUMENTS

2005/0092387 A1* 5/2005 Schorn .............. A61M 5/14276
141/18
2006/0271019 A1* 11/2006 Stoller ...................... A61F 5/44
604/544
2010/0114027 A1 5/2010 Jacobson et al.
2011/0060758 A1 3/2011 Schlotterbeck et al.

FOREIGN PATENT DOCUMENTS

SU 151438 A 4/1969
WO WO-97/27926 A2 8/1997

* cited by examiner

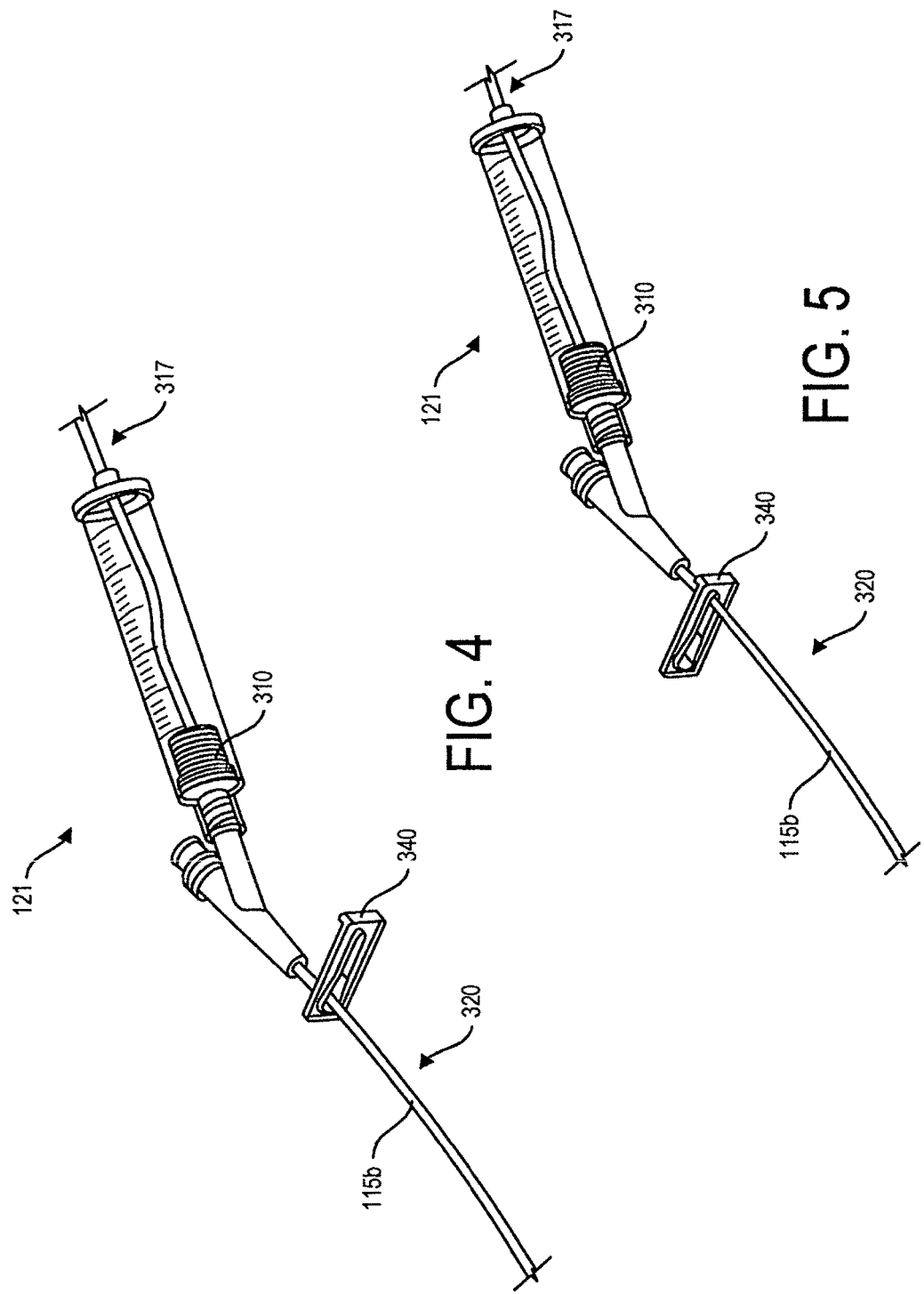

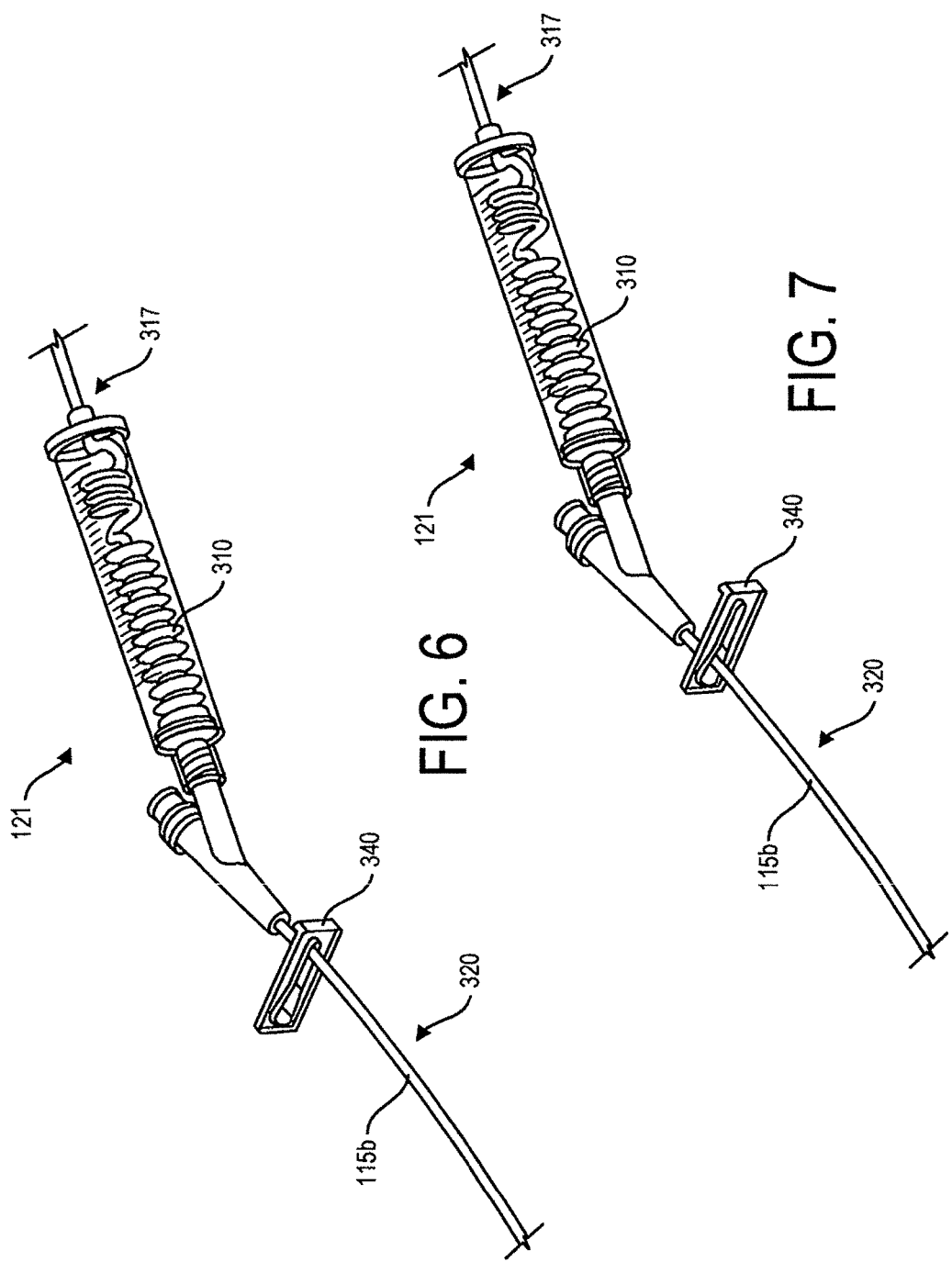

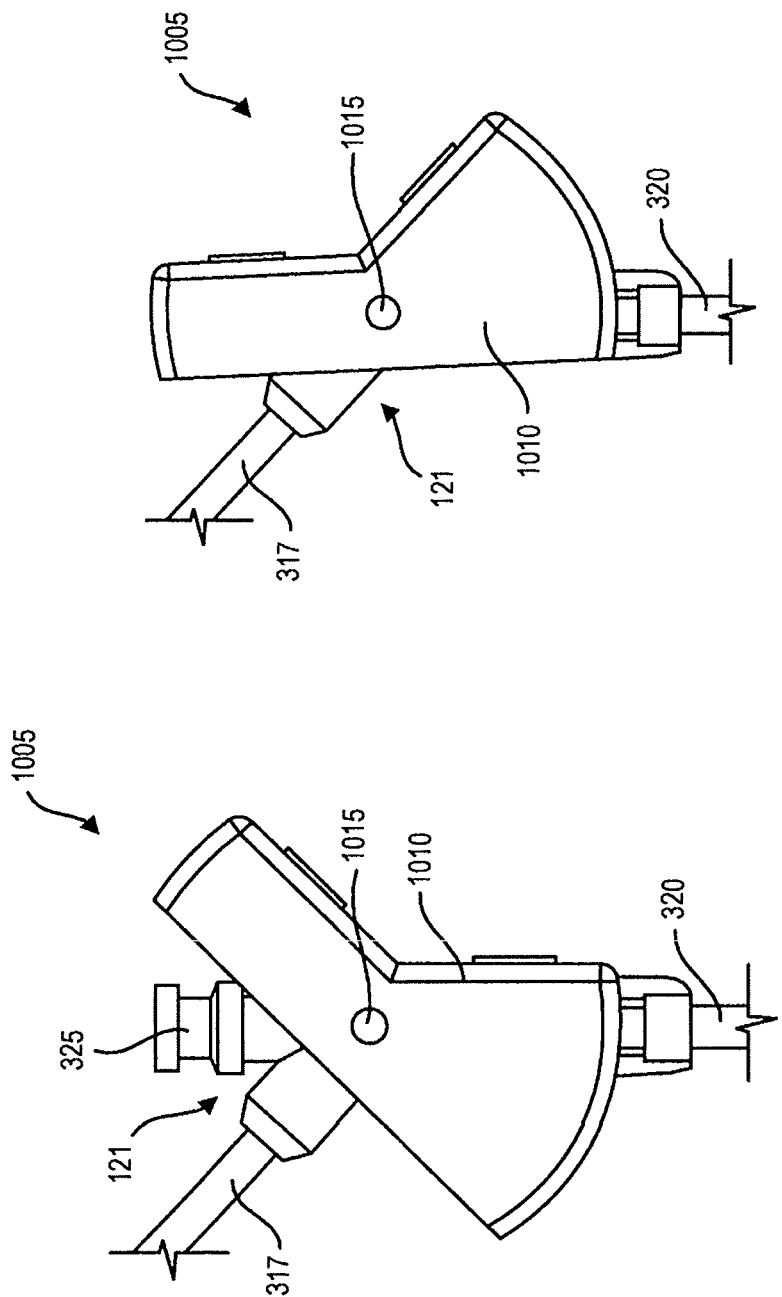

MICRO INFUSION DEVICE FOR DRUG DELIVERY

BACKGROUND

Intravenous (IV) fluid delivery pumps are used to deliver fluid to a patient or to draw out fluid from a patient's body. With respect to the delivery of fluid to the patient, delivery pumps and the associated control software are typically configured to deliver relatively large amounts of fluid over an extended period of time.

This may present problems when there is a requirement to deliver a small volume of fluid to a patient such as on the order of less than 2.5 milliliters of fluid (or in a range from about 0.1-5 mls) Under current procedures, a clinician can introduce the small volume of fluid into a primary fluid delivery line such as via a valve to the fluid delivery line. However, in order to do so the clinician must first detach the fluid line from the pump. Alternatively, a clinician could deliver a small volume of fluid by connecting a small volume syringe to a syringe pump. However, the small volume of fluid may be diluted in the fluid line or fluid from the small volume syringe may attached to the interior walls of the fluid line such that the proper dosage of fluid over time is not achieved.

SUMMARY

In view of the foregoing, there is a need for improved devices and methods for delivering small volumes of fluid to a patient using a fluid delivery pump. Described herein are medical fluid infusion systems including a pump system configured to deliver a fluid drug to a patient. The system includes a device and method for delivering a small amount of fluid, such as a drug, to a patient. The small volume of fluid may be for example, less than 5 ml of fluid although the volume may vary.

In one aspect, there is disclosed a device for introducing small volumes of fluid for delivery to a patient through a fluid line, comprising: a y-site comprising a first arm adapted to receive a syringe and a second arm fluidly connected to an upstream reservoir, the reservoir defining an internal volume adapted to receive a volume of fluid; and a fluid obstruction mechanism configured to selectably block flow of fluid from the reservoir toward the patient, wherein the fluid obstruction mechanism transitions between a first state that permits fluid flow from the reservoir toward the patient and a second state that directs fluid flow from the syringe into the reservoir while blocking fluid flow from the reservoir toward the patient.

In another aspect, there is disclosed a method of delivering a small volume of fluid into a fluid line attached to a patient, comprising: fluidly attaching a syringe to a first arm of a y-site located on the fluid line, the syringe containing a first volume of fluid, wherein the y-site additionally comprises a second arm fluidly connected to a reservoir; blocking fluid flow through the fluid line toward the patient at a location downstream of the syringe; actuating the syringe to inject the first volume of fluid into the fluid line such that the first volume of fluid flows toward the reservoir, thereby causing fluid to flow into the reservoir; and unblocking fluid flow through the fluid line to permit fluid to flow toward the patient.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIG. 4 shows the micro infuser attached to a fluid line with a clamp in an unclamped state.

FIG. 5 shows the micro infuser attached to a fluid line with a clamp in a clamped state.

FIG. 6 shows the micro infuser device with a clamped fluid line and no syringe attached.

FIG. 7 shows the micro infuser device with an unclamped fluid line and no syringe attached.

FIGS. 10-11 show an embodiment of a valve assembly.

Like reference symbols in the various drawings indicate like elements.

DETAILED DESCRIPTION

Described herein are medical fluid infusion systems including a pump system configured to deliver a fluid drug to a patient. The system includes a device and method for delivering a small amount of fluid, such as a drug, to a patient. The small volume of fluid may be for example, less than 5 ml of fluid although the volume may vary.

Figure 1A:
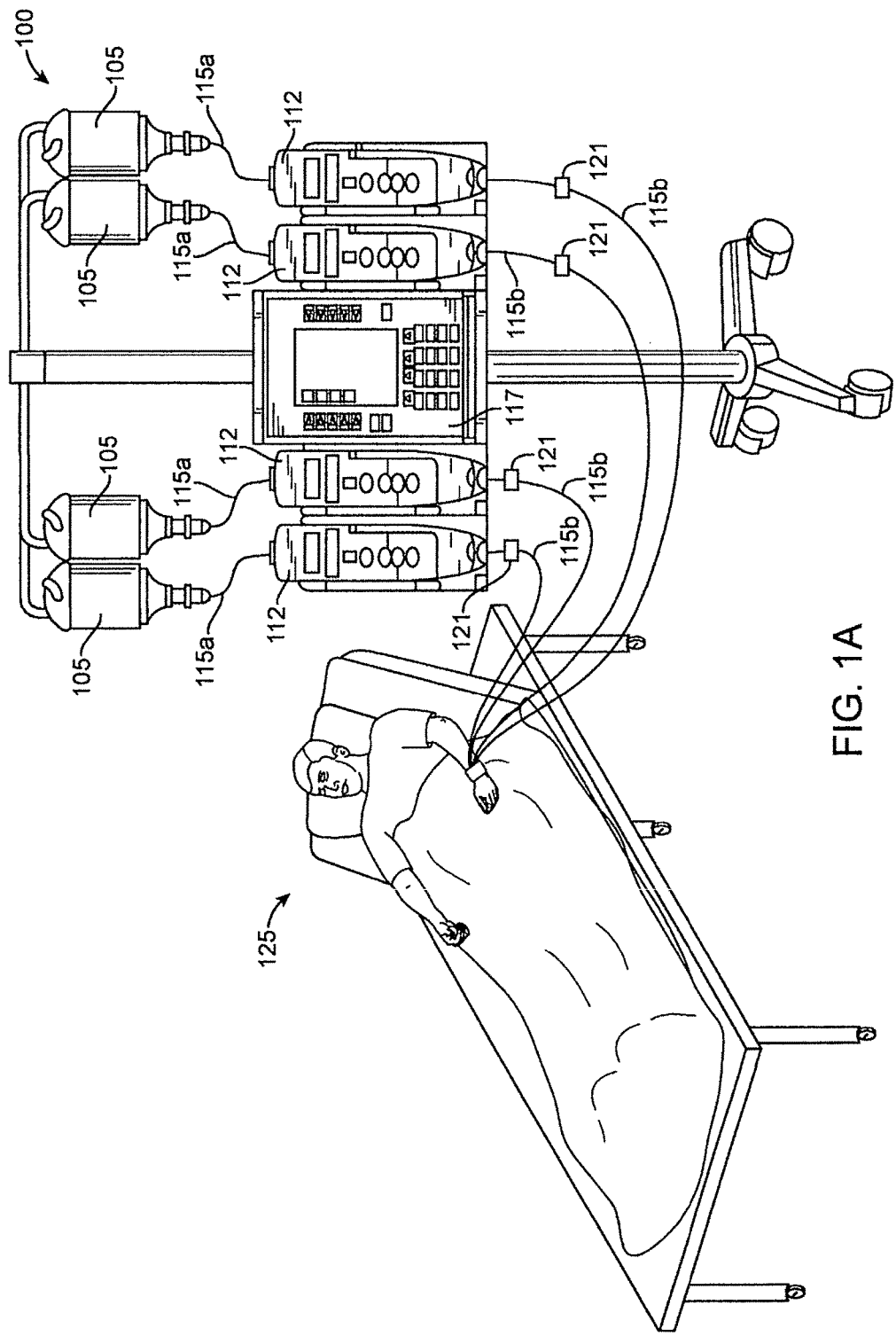
FIG. 1A is a schematic view of an infusion system according to one implementation.

FIG. 1A shows a schematic representation of a fluid infusion system 100. The fluid infusion system 100 is described herein in the context of being a bedside fluid drug infusion system for a patient although it should be appreciated that the features described herein may be used with any of a variety of fluid pumping systems and are not limited to drug infusion systems.

With reference to FIG. 1A, the infusion system 100 includes one or more fluid containers, such as intravenous (IV) bags 105, each of which is fluidly coupled to a respective fluid pump device 112 via a fluid conduit, such as a fluid line 115 having a lumen for flow of fluid. Each IV bag 105 contains a supply of fluid (such as a liquid drug or any other fluid) to be pumped to a patient. The pump device 112 is configured to pump fluid from the IV bag 105 toward a patient via a distal portion 115b of fluid line 115. The pump device 112 could be any commercially available infusion pump, such as the Alaris® Pump module (CareFusion, San Diego, Calif.) or the Plum A+™ Infusion System (Hospira, Lake Forest, Ill.) or any other infusion pump. In the illustrated embodiment, the system includes a plurality of pump devices 112 each with a corresponding IV bag 105 and fluid line 115. A central controller 117 is adapted to control the pump devices 112. It should be appreciated that the system can include any quantity of pump devices and corresponding IV bag and fluid line.

With reference still to FIG. 1A, each fluid line 115 has a proximal portion 115a upstream of the pump device 112 with the proximal portion 115a fluidly coupled to the IV bag 105 such as via a drip chamber. A distal portion 115B of each fluid line 115 downstream of the corresponding pump device 112 attaches to the patient 125 via an IV connection. A pumping mechanism of each pump device 112 acts on the respective fluid line to move fluid from the IV bag 105 to the patient. The pumping mechanism can vary and, for example, can be a peristaltic mechanism as found in the Alaris pump module or it could be a cassette based pumping system as found in the Plum A+ Infusion System. In either case the fluid line 115 forms a single fluid connection that extends from the IV bag 105 to the patient or may be interconnected with a cassette, such as the cassette described in U.S. Pat. No. 5,967,484 entitled "Intravenous Tube Occluder," but in any event the forms a single fluid pathway from the IV bag 105 to the patient.

The fluid line 115 may be formed of a single tube or may be formed of a series of tubes removably attached to one another, such as in an end-to-end manner using any of a variety of connectors such as Luer connectors. The fluid line 115 forms a continuous fluid lumen that provides a fluid pathway from the IV bag 105 toward the patient. This continuous fluid lumen may include any of a variety of components that facilitate or otherwise are used in connecting the tubes and/or pumping fluid, including, for example, the micro infuser device described herein, valves, filters, free-flow stop valves, pressure and air detection regions or components and access connectors, etc. Any of a variety of additional components may be used, including, for example, anti-free flow devices, pressure sensing components, air detection components, etc.

With reference still to FIG. 1A, a micro infuser device 121 is disposed along the distal portion 115b of each fluid line 115 such that fluid must flow through the micro infuser device 121 as it flows from the pump device 112 to the patient. As described in detail below, the micro-infuser device 121 is configured to allow the delivery of small volumes of fluid to the patient. In a first example embodiment, the micro infuser device 121 is a housing that defines a chamber in which an expandable, hollow member, such as a bellows, is positioned. The bellows defines an internal chamber of variable volume into which a fluid can be injected using a syringe for pumping to the patient, as described below with reference to FIG. 2.

Figure 1B:
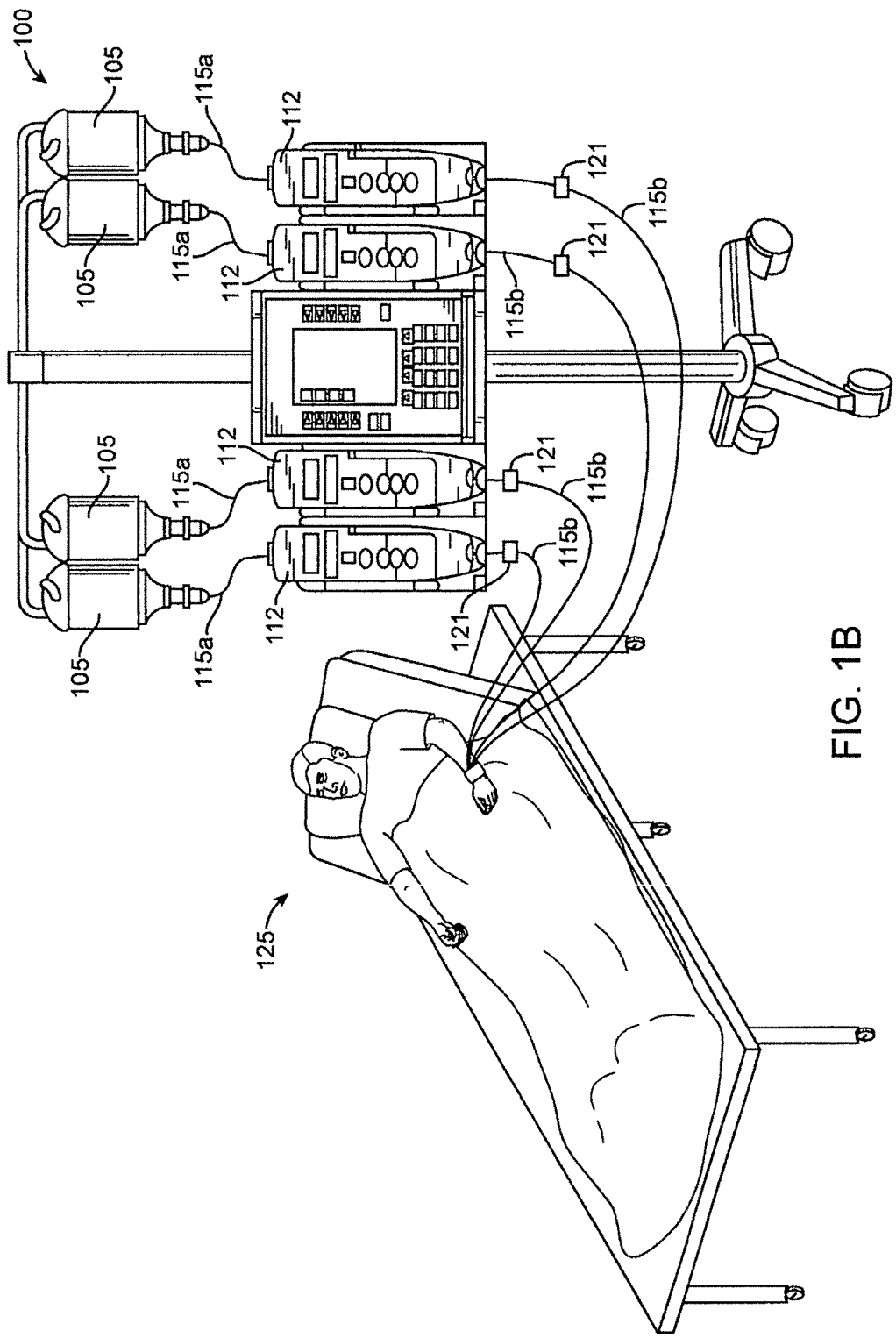
FIG. 1B is a schematic view of an infusion system according to another implementation.

FIG. 1B shows another embodiment wherein like reference numerals refer to like items as FIG. 1B. In this embodiment, the micro-infuser device 121 includes a fillable reservoir, as described in more detail below with reference to FIG. 12.

For each fluid line, the micro infuser device 121 may be located along the fluid line 121 at any position between the pump device 112 and the patient. For example, the micro infuser device 121 may be located very near or at the pump device 112 or very near the patient as long as fluid passes through the micro infuser device 112 as it is pumped to the patient via the pump device 112. In another embodiment, a micro infuser device 121 may be detachably coupled attached to the distal portion 115b of fluid line 115 downstream of the pump device 112 for example with the use of Luer connectors at the y-site of the infusion set.

Micro Infuser Device

Figure 2:
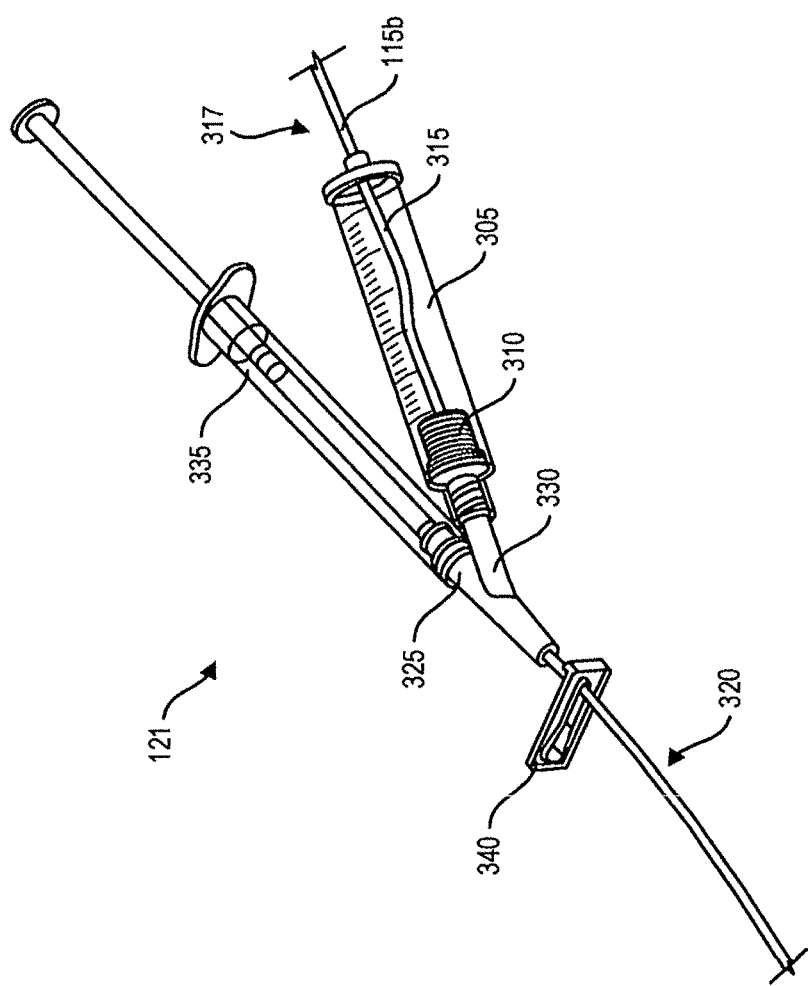
FIGS. 2 and 3 shows an embodiment of a micro infuser device.
Figure 3:
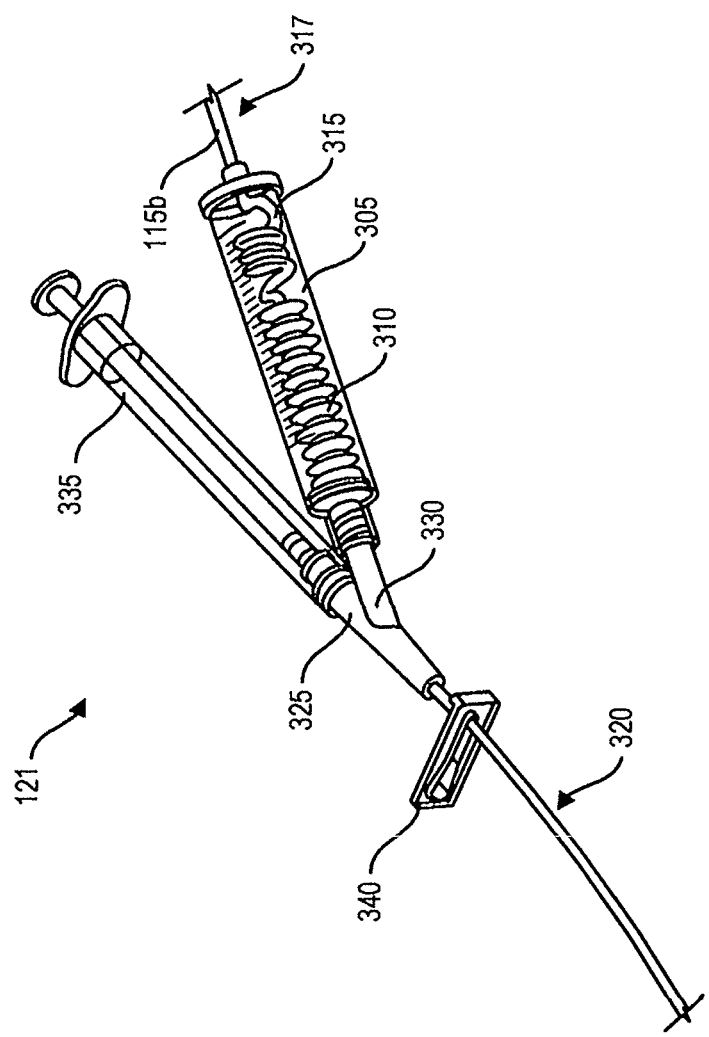

FIGS. 2 and 3 show perspective views of a first embodiment of the micro infuser device 121 attached to the distal portion 115b of fluid line 115. The micro infuser device 121 includes a housing 305 that defines a chamber in which an expandable, hollow member, such as a bellows 310, is positioned in series with a tubing 315. The bellows defines an internal chamber of variable volume (including a maximum volume) into which a fluid can be injected using a syringe 335 for pumping to the patient.

The bellows 310 is fluidly coupled to the tubing 315. The bellows 310 and tubing 315 each define internal flow pathways that are attached and that fluidly attach an upstream region 317 of the distal portion 115b of fluid line 115 to a downstream region 320 of the distal portion 115b of fluid line 115. In this manner, fluid (such as a drug) must flow through the tubing 315 and bellows 310 in order to flow from the upstream region 317 to the downstream region 320 of the distal portion 115b of fluid line 115. A downstream region of the housing 305 leads to a y-site with a first arm 325 and a second arm 330 that both have lumens that feed into the downstream region 320 of the distal portion 115b of fluid line 115. The y-site (or y-arm) includes two separate tubings with each tubing being fed by a separate fluid source and wherein both tubings feed into a single tubing. The first arm 325 is configured to be detachably coupled to the syringe 335 such as via a Luer connection. The second arm 330 is fluidly coupled to the flow pathway of the bellows 310 and tubing 315.

The bellows 310 can transition from a first, contracted state to a second, expanded state. As described below, the bellows 310 is initially in the contracted state and then expands toward the expanded state as a small volume of fluid is injected therein using the syringe 335. FIG. 2 shows the bellows in the contracted state wherein pleats of the bellows are drawn together or contracted such that an internal volume of the bellows is relatively small (with respect to the expanded state). FIG. 3 shows the bellows in the expanded state wherein the pleats of the bellows are expanded outward such that internal volume of the bellows is relatively large compared to the contracted state. The contracted state is the default state of the bellows 310.

A flow restrictor or blocker, such as a clamp 340, is positioned on the downstream region 320 of the distal portion 115b of fluid line 115 at a location downstream of the bellows 310. The clamp 340 can be moved between an unclamped position and a clamped position. In the clamped position (as shown in FIGS. 2 and 3), the clamp 340 blocks flow through the downstream region 320 of the distal portion 115b of fluid line 115. In the unclamped position (shown in FIG. 4), the clamp 340 does not impede or does not otherwise restrict flow through the downstream region 320. Thus, when the clamp 340 is in the clamped position, the syringe 335 can be actuated to cause a volume of fluid in the syringe 335 to flow out of the syringe 335 and into the bellows 310 via the first arm 325 and second arm 330 of the y-site. It should be appreciated that any of a variety of mechanisms can be used to block fluid flow through the downstream region 320 and that some examples are described herein.

A method of using the micro infuser device 121 is now described. The method may be performed by a clinician for example. With reference to FIG. 4, the micro infuser device 121 is initially attached to the distal portion 115b of fluid line 115 with the clamp 340 in the unclamped state. As mentioned, the downstream region 320 of the fluid line flows toward and is attached to the patient. Thus, with the clamp 340 in the unclamped state, fluid is free to flow toward the patient via the distal portion 115b of fluid line 115. The distal portion 115b of fluid line 115 is primed with fluid prior to use of the micro infuser device 121. As shown in FIG. 5, the clamp 340 is moved to the clamped state such that it blocks fluid flow through the downstream region 320 of the distal portion 115b of fluid line 115. Note that the bellows 310 is in the contracted state, which is the default state of the bellows 310. As mentioned, any of a variety of mechanisms can be used as a means to clamp the downstream region 320 of the distal portion 115b of fluid line 115.

With reference again to FIG. 2, in a next step the syringe 335 is attached to the first arm 325 of the y-site. The syringe 335 has previously been loaded with a predetermined volume of fluid. The syringe 335 is then actuated such as by depressing a plunger on the syringe to cause the volume of fluid to flow out of the syringe and into the first arm 325. As mentioned, the clamp 340 blocks flow through the downstream region 320 of the distal portion 115b of fluid line 115 such that the fluid from the syringe 335 must flow through the second arm 330 of the y-site and into an expanding bellows 310.

The flow of fluid from the syringe 335 causes the bellows 310 to expand and transition to the expanded state, as shown in FIG. 3. In this state, the bellows 310 now contains the volume of fluid that has been pushed from the syringe 335. Also, the tubing 315 can coil up within the housing 305 as the bellows expands, as shown in FIG. 3. The bellows 310 thus acts as a chamber that contains a volume of fluid from the syringe 335. The bellows 310 can continue to expand as fluid is injected therein from the syringe 335. The bellows 310 can expand to a maximum expanded state that represents the maximum volume of fluid that it can hold. Once expanded, the bellows 310 remains in its expanded state and has no tendency to return to the contracted state after expansion.

With the bellows 310 filled with the volume of fluid, the syringe 310 is then detached from the micro infuser device 121 while the clamp 340 is still in the clamped position.

FIG. 6 shows the micro infuser device 121 with the bellows 310 expanded and the syringe absent from the device. As shown in FIG. 7, the clamp 340 is then transitioned to the unclamped position such that it no longer blocks fluid flow through the downstream region 320. Fluid is thus permitted to flow through the downstream region 320 of the distal portion 115b of fluid line 115 from the upstream region 317 as the pump device 112 pumps. The pump device 112 (FIG. 1) can then be activated to pump fluid toward the patient via the distal portion 115b of fluid line 115. As the pump device 112 pumps, it pushes the volume of fluid in the bellows 310 downstream toward the patient. This would include the volume of fluid that was injected into the bellows 310 using the syringe 335.

The aforementioned process can be repeated with additional syringes containing small volumes of fluid until the bellows expands to its maximum volume. At this point, the syringe can no longer be used to inject fluid into the bellows.

In another embodiment, the micro infuser device 121 includes a valve in place of the clamp 340 so as to eliminate the need for the clamp 340. The valve automatically transitions between (1) a first state that blocks flow from the micro infuser device 121 into the downstream region 320 of the distal portion 115b of fluid line 115 when a syringe 335 is attached to the y-site of the micro infuser device 121; and (2) a second state that permits fluid to flow from the micro infuser device 121 into the downstream region 320 of the distal portion 115b of fluid line 115 when no syringe 335 is attached to the y-site of the micro infuser device 121. The valve transitions between the first and second state automatically based on whether the syringe is attached to the y-site of the micro infuser device 121.

Figure 8:
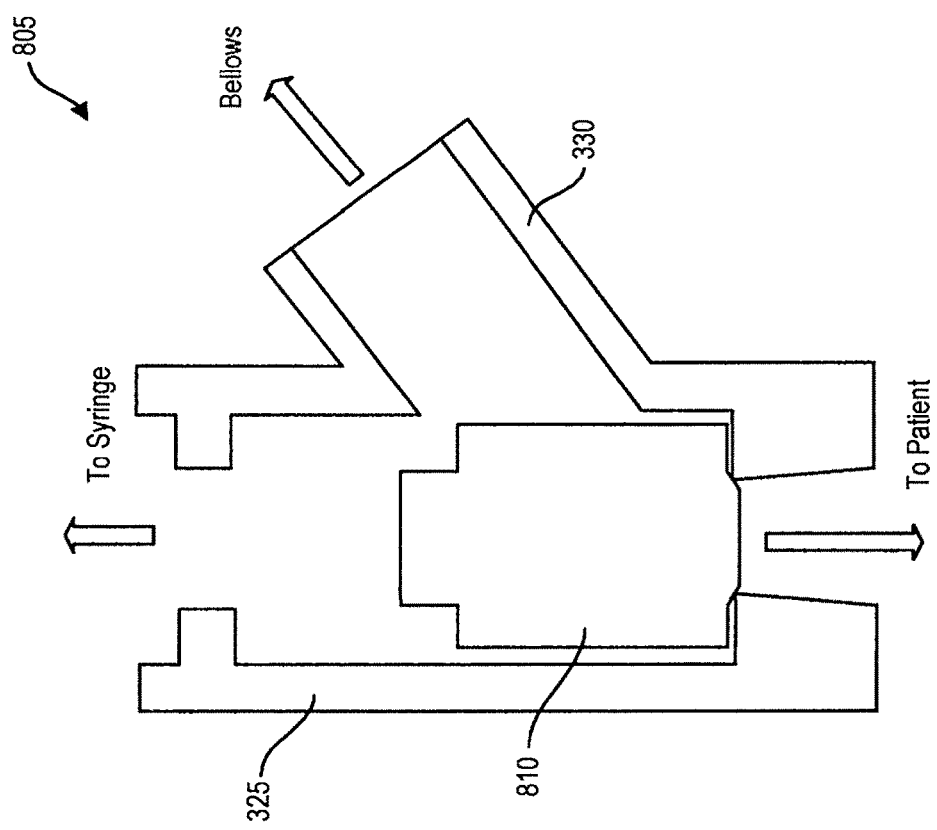
FIGS. 8 and 9 show a schematic representation of a valve for use with the micro infuser device.

FIG. 8 shows a schematic, cross-sectional view of the valve 805, which is incorporated in the y-site of the micro infuser device 121. FIG. 8 shows the valve 805 in the first state wherein it blocks fluid flow from the micro infuser device 121 toward the downstream region of the distal portion 115b of fluid line 115 (i.e., blocks flow toward the patient from the micro infuser device 121). The valve 805 includes a blocking member 810 that is pushed by the syringe into a position that blocks fluid flow from the micro infuser 121 toward the patient. The syringe 335, when attached to the first arm 325 of the y-site, pushes the blocking member 810 into the blocking position. For example, when the syringe is attached to the micro infuser device 121, a distal end of the syringe 335 pushes the blocking member 810 into a position that blocks fluid flow out of the y-site of the micro infuser device 121 as shown in FIG. 8. However, the blocking member 810 leaves an opening such that fluid flow can occur from the first arm 325 to the second arm 330 and into the bellows 310. Thus, when the syringe is actuated, fluid from the syringe automatically flows through the y-site and into the bellows of the micro infuser device 121.

Figure 9:
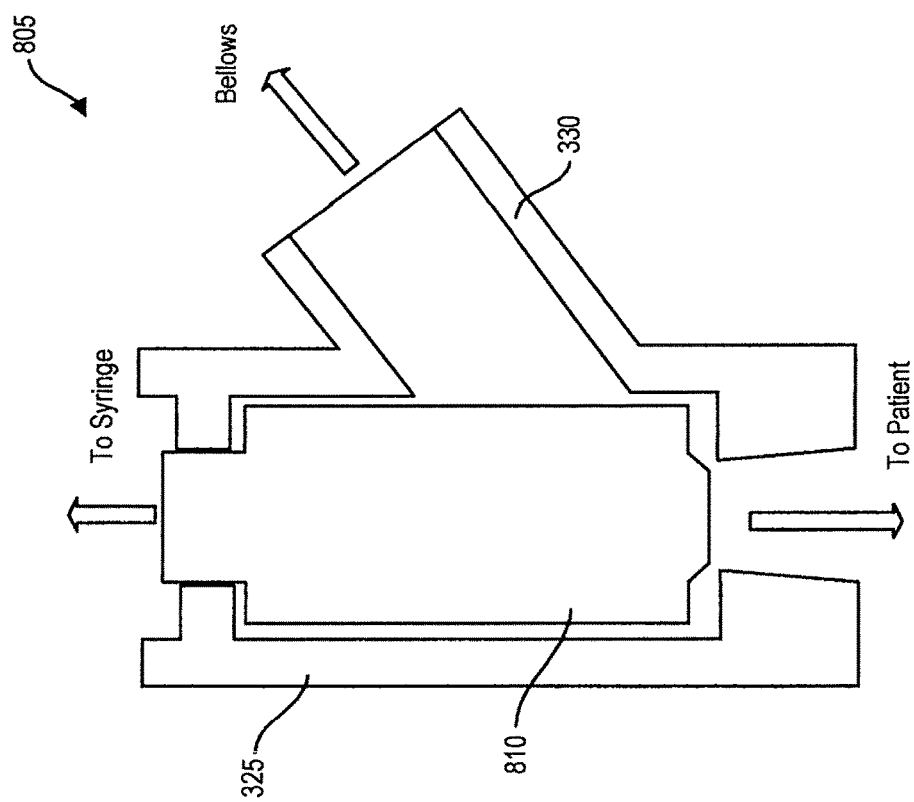

FIG. 9 shows the valve 805 in the second state wherein it permits fluid to flow from the micro infuser device 121 into the downstream region 320 of the distal portion 115b of fluid line 115. Note that in FIG. 9 the blocking member 810 is positioned such that it leaves an opening for fluid to flow from the bellows 310 toward the patient via the second arm 330. The blocking member automatically transitions to the second state when the syringe is detached from the micro infuser device 121. Thus, with the syringe detached, fluid flow through the micro infuser device and into the downstream region 320 of the distal portion 115b of fluid line 115 when the pump device 112 is active.

FIG. 10 shows version of a valve assembly 1005 that can be used with the micro infuser device 121 to control flow through the downstream region 320 of the distal portion 115b of fluid line 115 based on whether the syringe is attached to the micro infuser device 112. The valve assembly 1005 mechanically transitions between (1) a first state that blocks flow from the micro infuser device 121 into the downstream region 320 of the distal portion 115b of fluid line 115 and permits the syringe to be attached to the micro infuser device 112; and (2) a second state that permits fluid to flow from the micro infuser device 121 and prevents the syringe from being attached to the micro infuser device 112. The valve assembly 1005 includes a shroud 1010 that moves between the first and second states.

FIG. 10 shows the valve assembly 1005 in the first state that blocks flow from the micro infuser device 121 into the downstream region 320 of the distal portion 115b of fluid line 115 and permits the syringe to be attached to the y-site of the micro infuser device 121. The shroud 1010 is pivotably attached to the y-site of the micro infuser device 121 such that it can rotate about a pin 1015. In the first state shown in FIG. 10, the shroud 1010 is positioned, sized and shaped such that the first arm 325 of the y-site is exposed, thereby permitting the syringe to be attached to the first arm 325 of the micro infuser device 121. When in the first state, a bottom region of the shroud 1010 pinches or otherwise obstructs the downstream region 320 of the distal portion 115b of fluid line 115 to prevent fluid flow therethrough when the syringe is attached to the y-site.

The shroud 1010 can pivot to the second state (which is the default state of the valve assembly 1005.) In the second state (shown in FIG. 11) the shroud 1010 is positioned, sized and shaped such that it covers the first arm 325, thereby preventing the syringe from being attached to the first arm 325. In addition, the shroud 1010 does not block or inhibit flow through the downstream region 320 of the distal portion 115b of fluid line 115 when in the second state.

Figure 12:
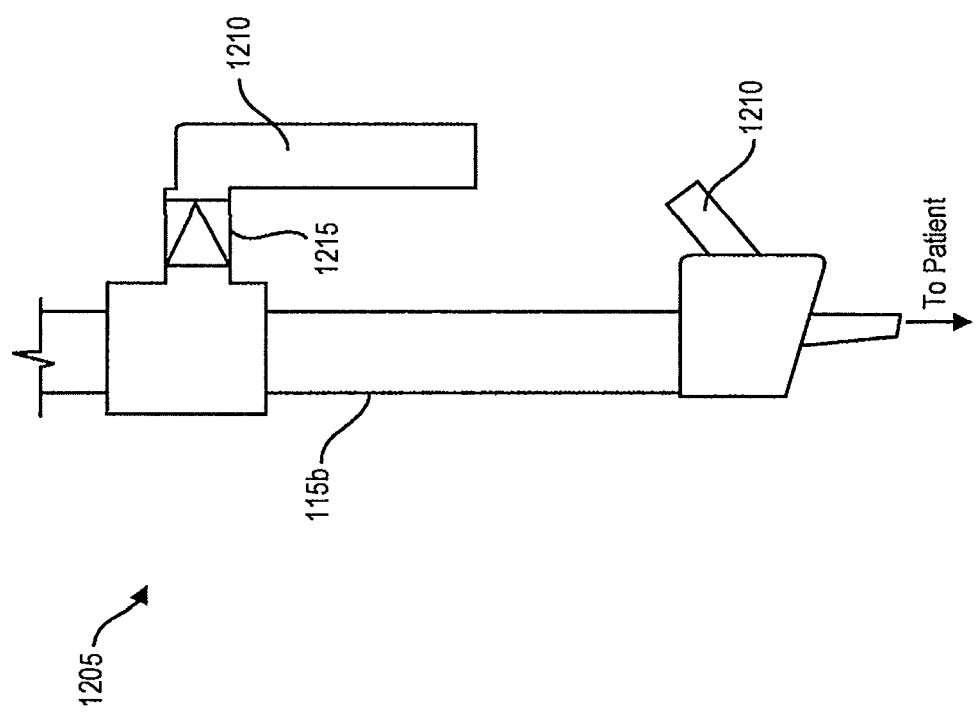
FIG. 12 shows another embodiment of the micro infuser device.

FIG. 12 shows an alternate embodiment of a micro infuser device 1205 that couples to the distal portion 115b of fluid line 115 connected to the patient. The micro infuser device 1205 includes a port 1210, which may be a y-site for example, in the downstream region of the fluid line. The port includes two inlets including a first inlet that can be removably attached to a syringe and a second inlet from the distal portion 115b of fluid line 115. An outlet of the port 1210 flows toward the patient. The port 1210 is removably attachable to a syringe that can be used to inject fluid into the distal portion 115b of fluid line 115. The port 1210 can include any type of attachment mechanism for removably attaching to a syringe. The embodiment of FIG. 12 is not necessarily shown to scale. The fluid line 115 and port 1210 can vary in structural configuration including cross-sectional shape.

With reference still to FIG. 12, a reservoir 1210 fluidly communicates with the distal portion 115b of fluid line 115 upstream of the location of the port 1210. The reservoir 1210 defines an internal chamber that is sized to contain a predetermined volume of fluid, which predetermined volume of fluid is equal to a maximum amount of fluid that can be injected into the distal portion 115b of fluid line 115 using the syringe, as described further below. A check valve 1215 is positioned in a fluid line that extends out of series with the distal portion 115b of fluid line 115 at the junction between the reservoir 1210 and the distal portion 115b of fluid line 115. The check valve 1215 permits flow only in one direction—into the reservoir 120—and blocks flow in a direction from the reservoir into the distal portion 115b of fluid line 115. The check valve opens for flow into the reservoir at a predetermined cracking pressure. In an embodiment the cracking pressure is in the range of approximately 20 to 30 psi. In an embodiment, the reservoir 1210 is removably attached to the distal portion 115b of fluid line 115 such that the reservoir 1210 can be replaced. The check valve 1215 may be any type of check valve including, for example, a duck bill valve. In an embodiment, the reservoir 1210 and/or the check valve 1215 is removably attached to the flow line 115.

In use, a clinician injects a volume of fluid into the distal portion 115b of fluid line 115 using a syringe attached to the port 1210. As fluid is injected, a pressure differential forms in the fluid line to push fluid already in the distal portion 115b of fluid line 115 toward the reservoir 1210. This causes fluid pressure to rise sufficient to open the check valve 1215 such that fluid flows into the reservoir 1210 from the distal portion 115b of fluid line 115 as a result of the syringe injecting fluid. The amount of fluid that flows into the reservoir is equal to the amount of fluid that the clinician injected into the fluid line using the syringe. The clinician can continue to inject small volumes of fluid into the reservoir 1210 until the reservoir completely fills, at which point the reservoir 1210 may be detached from the distal portion 115b of fluid line 115. The clinician may then attach a second reservoir to the distal portion 115b of fluid line 115. Or the valve 125 may be closed or otherwise turned off so that fluid can no longer flow through the valve.

It should also be appreciated that the described infusion systems are not limited to intravenous infusions, but can be used for any number of infusion types to a patient through a catheter including but not limited to parenteral, intraarterial, intracardiac, intraosseous, intramuscular, intrathecal, intraperitoneal, epidural, intracerebral, gastrointestinal, and the like. In addition, the infusion systems described herein can be used in conjunction with any of a variety of electronic and/or software medication management systems, such as the system described in U.S. Patent Publication 2011/0060758 to Schlotterbeck. U.S. Patent Publication 2011/0060758 is incorporated herein by reference in its entirety.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A device for introducing small volumes of fluid for delivery to a patient through a fluid line, comprising:
    a y-site comprising a first arm adapted to receive a syringe and a second arm fluidly connected to an upstream reservoir, the reservoir defining an internal volume adapted to receive a volume of fluid; and
    a fluid obstruction mechanism inside the y-site, the fluid obstruction mechanism configured to selectably block flow of fluid from the reservoir toward the patient, wherein the fluid obstruction mechanism transitions between a first state that permits fluid flow from the reservoir toward the patient and a second state that directs fluid flow from the syringe into the reservoir while blocking fluid flow from the reservoir toward the patient, wherein the syringe pushes the fluid obstruction mechanism to the second state when the syringe is inserted into the y-site.

2. A device as in claim 1, wherein the reservoir is an expandable bellows.

3. A device as in claim 2, wherein the expandable bellows can expand to define a maximum internal volume of the reservoir.

4. A device as in claim 2, wherein the bellows is contained within a housing.

5. A device as in claim 2, further comprising a housing encasing the reservoir.

6. A device as in claim 5, further comprising a coilable tubing within the housing and attached to the distal end of the reservoir.

7. A device as in claim 5, further comprising a pump coupled to the fluid line.

8. A device as in claim 1, wherein the expandable bellows remains in an expanded state once it expands.

9. A device as in claim 1, wherein the expandable bellows has a default contracted state.

10. A device as in claim 1, wherein the reservoir has a fixed volume.

11. A method of delivering a small volume of fluid into a fluid line attached to a patient, comprising:
    fluidly attaching a syringe to a first arm of a y-site located on the fluid line, the syringe containing a first volume of fluid, wherein the y-site additionally comprises a second arm fluidly connected to a reservoir;

causing the syringe to push an obstruction mechanism inside the y-site so that the obstruction mechanism blocks fluid flow through the fluid line toward the patient at a location downstream of the syringe;

actuating the syringe to inject the first volume of fluid into the fluid line such that the first volume of fluid flows toward the reservoir, thereby causing fluid to flow into the reservoir; and unblocking fluid flow through the fluid line to permit fluid to flow toward the patient.

12. A method as in claim 11, wherein the reservoir is an expandable bellows and wherein the bellows expands when the syringe injects the first volume of fluid.

13. A method as in claim 11, further comprising repeating the steps of claim 11 until the reservoir fills to a maximum volume.

14. A method as in claim 11, further comprising activating a pump to cause the first volume of fluid to flow through the fluid line toward the patient.

15. A method as in claim 11, wherein fluid flow is automatically blocked through the fluid line toward the patient when the syringe is fluidly attached to the first arm of the y-site.

* * * * *